United States Patent [19]

Combret et al.

[11] Patent Number: 5,113,007
[45] Date of Patent: May 12, 1992

[54] DIENOXYSILANES

[75] Inventors: Jean-Claude Combret, Rouen; Jean-Louis Klein, Mont Saint-Aignan; Joël Le Gaillard, Rouen, all of France

[73] Assignee: Universite de Rouen, France

[21] Appl. No.: 610,827

[22] Filed: Nov. 8, 1990

[30] Foreign Application Priority Data

Nov. 9, 1989 [FR] France .................. 89 14882

[51] Int. Cl.$^5$ .......................... C07F 7/08; C07F 7/12; C07F 7/10
[52] U.S. Cl. ........................ 556/482; 556/470; 556/488; 544/106; 546/14; 548/406
[58] Field of Search ............. 556/413, 470, 482, 488; 544/106; 546/14; 548/406; 568/142, 485

[56] References Cited

U.S. PATENT DOCUMENTS 4,772,714 9/1988 Tanaka et al. .................. 546/14 X
4,785,126 11/1988 Bruno .......................... 556/482 X
4,831,172 5/1989 Hahn et al. .................... 556/482 X

*Primary Examiner*—Arthur C. Prescott
*Attorney, Agent, or Firm*—Ostrolenk, Faber, Gerb & Soffen

[57] ABSTRACT

New dienoxysilanes of the general formula:

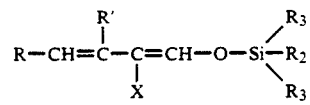

and new α-halo α-ethylene aldehydes to which they give access, having the general formula:

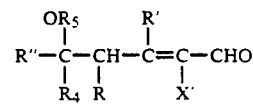

These new compounds constitute important synthesis intermediates opening a new path for access to macrolides such as pyrenophorine, norpyrenophorine or vermiculine.

10 Claims, No Drawings

DIENOXYSILANES

The present invention relates to new dienoxysilanes, the method of obtaining them, the new α-halo α-ethylene aldehydes to which they give access, and the method of obtaining these new α-halo α-ethylene aldehydes.

The functional dienoxysilanes which constitute the first object of the present invention are synthesis intermediates of great interest, since they open up new access to macrolides such as pyrenophorine, norpyrenophorine and vermiculine, which have fungicidal properties.

The dienoxysilanes which constitute the first object of the present invention can be represented by the general formula:

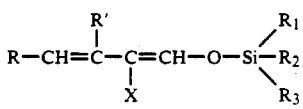

in which R is a hydrogen atom or a linear alkyl radical having 1 to 4 carbon atoms, R' is a hydrogen atom or a methyl radical, $R_1$, $R_2$, and $R_3$ each designates an alkyl radical containing 1 to 4 carbon atoms or an aryl radical, and X designates a halogen atom, a dialkylamino radical each of the alkyl groups of which contain 1 to 4 carbon atoms, or a pyrrolidino, piperidino or morpholino radical, with the condition that R' can be a methyl radical only when R is a hydrogen atom.

The dienoxysilanes of the invention can be obtained from a trialkylchlorosilane and an α-substituted α-ethylene aldehyde in accordance with the following general reaction:

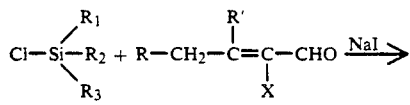

in which different substituents have the same meaning as above.

This reaction, which is known for the obtaining of non-functional dienoxysilanes, must however be carried out in an anhydrous medium which is retained up to the isolation of the dienoxysilanes, in view of the sensitivity of these compounds to hydrolysis.

The method of obtaining the dienoxysilanes of the invention thus comprises, in a first step, the carrying out of this reaction, which is effected at room temperature in an inert atmosphere with agitation in an anhydrous solvent such as acetonitrile and in the presence of a weak base which may be a tertiary amine, such as triethylamine, pyridine, N-ethylmorpholine or 4-dimethylaminopyridine.

In this first step of the process of the invention, the trialkylchlorosilane and the α-substituted α-ethylene aldehyde are used in substantially equimolecular quantities, as are the triethylamine and the sodium iodide, which are, however, employed in substantially higher molar quantities.

The second step of the process of the invention consists in extracting the dienoxysilane from the reaction mixture, which extraction may be carried out by means of a nonpolar solvent such as petroleum ether, pentane, hexane or cyclohexane.

The yield of the reaction is about 75 to 90% and the products obtained are sufficiently pure not to require further purification.

Among the dienoxysilanes of the invention, those which are α-halogenated have the property of reacting selectively at 4 with electrophilic compounds, and this property can advantageously be used to obtain the α-halo α-ethylene aldehydes which constitute another object of the present invention.

The α-halo α-ethylene aldehydes in accordance with the invention have the general formula:

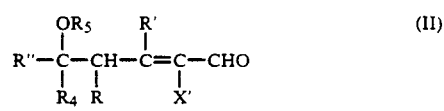

in which R and R' have the same definition as above, X' is a halogen atom, R" an alkyl, aryl or heteroaryl radical, an alkylethylene or arylethylene radical, or a methoxy or ethoxy radical, $R_4$ is a hydrogen atom or a methyl radical, and $R_5$ is a hydrogen atom or a methyl or ethyl radical.

The α-halo α-ethylene aldehydes of Formula II may be obtained, by a method which also constitutes an object of the present invention, by action of an aldehyde, acetal or orthoformate on a halogenated dienoxysilane of the general formula:

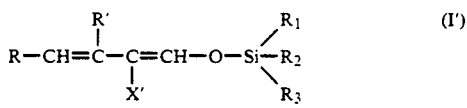

in which the different substituents have the same definition as above.

The reaction is carried out at a temperature of 0° to 20° C. in an anhydrous solvent such as dichloromethane, in an inert atmosphere in the presence of a Lewis acid catalyst which may be titanium tetrachloride, zinc dichloride or zinc dibromide, the starting products being used in substantially equimolecular quantities.

In accordance with a first embodiment of the method of the invention, a dienoxysilane of formula I' is subjected to the action of an aldehyde of the general formula R"CHO, the reaction leading to the obtaining of an α-halo α-ethylene aldehyde of the formula:

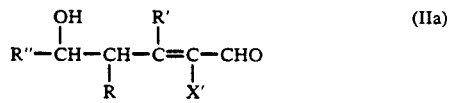

in which R, R', R" and X' have the same meanings as above.

The reaction time varies from 2 to 3 hours at 0° C. or at room temperature, and the yield of product IIa is 80 to 90%.

It should be noted that, in accordance with the structure of the dienoxysilane I' and the nature of the aldehyde used, the compound IIa can be obtained in mixture with the corresponding siloxane and, in certain cases, the reaction leads to the obtaining of this siloxane by itself, the hydrolysis thereof supplying the compound IIa.

In accordance with a second embodiment of the method of the invention, a dienoxysilane of formula I' is subjected to the action of an aldehyde or ketone acetal of the general formula:

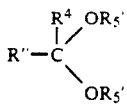

this reaction leading to the obtaining of an α-halo α-ethylene aldehyde of the formula:

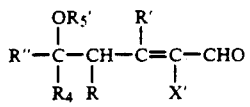

in which the substituents R, R', R", R$_4$ and X' have the same meaning as above, and R'$_5$ is a methyl or ethyl radical.

The reaction time varies from 10 minutes to 4 hours at room temperature, and the yield of product IIb is about 80%.

According to a third embodiment of the method of the invention, a dienoxysilane of formula I' is subjected to the action of an orthoformate of the general formula HC (OR'$_5$)$_3$, this reaction leading to the obtaining of an α-halo α-ethylene aldehyde of the formula

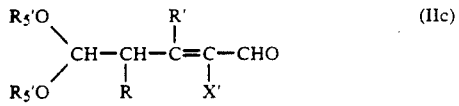

in which the substituents have the same meaning as above.

The reaction time is about 24 hours at room temperature, and the yield of product IIc is about 70%.

In all cases, the α-halo α-ethylene aldehyde is isolated from the reaction medium after addition of water, the aqueous phase being extracted by means of dichloromethane and the organic phase being dried over anhydrous magnesium sulfate before evaporation of the solvent, leading to the obtaining of the α-halo α-ethylene aldehyde.

The products obtained can then be distilled or purified by column chromatography.

The α-halo α-ethylene aldehydes of formula II are also important synthesis intermediates, constituting one of the steps of the new procedure for access to macrolides provided by the dienoxysilanes of formula I.

The following examples are given by way of illustration of the present invention, it being understood that they in no may limit the invention.

EXAMPLE 1

Preparation of 2-bromo-1-trimethylsiloxybuta-1,3-diene 5.5 g of sodium iodide are placed in a stainless steel crucible and heated by means of a Bunsen burner to 200° C. for 15 minutes, with constant agitation of the solid. 4.5 g (30 mmoles) of this hot sodium iodide are introduced into 40 cc of acetonitrile which has been dried by distillation over calcium hydride.

Furthermore, 2.98 g (20 mmoles) of 2-bromobut-2-enal and 3 g (30 mmoles) of triethylamine are introduced into a 250 ml container. At room temperature, in a nitrogen atmosphere with agitation, there is added 1.63 g (30 mmoles) of chlorotrimethylsilane followed, drop by drop, by the solution of sodium iodide in acetonitrile which was previously prepared. After reaction for 90 minutes, 60 cc of anhydrous petroleum ether (petroleum ether 40-60) are added and agitation is effected for 30 minutes. The precipitate which forms is filtered off under a nitrogen atmosphere and then washed twice with 30 ml of anhydrous petroleum ether. The upper phase of the filtrate (petroleum ether) is collected and the lower phase (acetonitrile) extracted 3 times with, in each case, 30 ml of petroleum ether. The petroleum ether fractions are collected and 5 g of anhydrous magnesium sulfate added thereto. Filtration is effected over fritted glass and the solvent eliminated by vacuum distillation (rotary evaporator) in an inert atmosphere. The residue obtained is diluted in 80 cc of anhydrous ethyl ether; the precipitate is filtered and the solvent evaporated under an atmosphere of nitrogen. 3.76 g of product are obtained, representing a yield of 85%. Purity (GC) of the product obtained is 98% and its structure is confirmed by nuclear magnetic resonance and mass spectrometry.

EXAMPLE 2

Preparation of 2-morpholino-1-trimethylsiloxybut-1,3-diene

Proceeding in the same manner as in Example 1, and with the same proportions of the different products, one obtains, starting from 3.1 g of 2-morpholinobut-2-enal, 3.4 g of product, which represents a yield of 75%. The purity of the product obtained is 98% (GC) and its structure is confirmed by NMR analysis.

EXAMPLE 3

Preparation of 2-bromo-5-ethoxyhex-2-enal

A solution of 2.21 g (10 mmoles) of 2-bromo-1-trimethylsiloxybut-1,3-diene in 30 ml of anhydrous dichloromethane are introduced into a 100 ml reactor traversed by a stream of nitrogen. 1.18 g (about 11 mmoles) of 1,1-diethoxyethane are slowly added and then 100 mg of anhydrous zinc bromide. After reaction for 10 minutes, 20 ml of water are added, the organic phase is collected, and the aqueous phase is extracted with 20 ml of dichloromethane. The dichloromethane fractions are combined and dried with 5 g of anhydrous magnesium sulfate. The solvent is eliminated by vacuum evaporation and the residue distilled, the boiling point of the product being 66° C. under 0.15 mm Hg. 1.72 g of product are obtained, representing a yield of 78%. The structure of the product obtained is confirmed by NMR analysis and mass spectrometry.

EXAMPLE 4

Preparation of 2-bromo-5-ethoxy-7-phenylhept-2,6-dienal

One starts with 2.21 g of 2-bromo-1-trimethylsiloxybut-1,3-diene and 2.06 g of 3,3-diethoxyl-1-phenyl-prop-1-ene and proceeds in the same manner as in Example 3, except that the reaction is carried out for two hours.

The product of the reaction is purified by liquid phase chromatography on a silica column, the eluant being a mixture of petroleum ether and ethyl acetate (90:10 by volume).

2.63 g of product are obtained, representing a yield of 85%. The structure of the product is confirmed by NMR analysis.

EXAMPLE 5

Preparation of 2-bromo-5,5-dimethoxypent-2-enal

One starts with 2.21 g of 2-bromo-1-trimethylsiloxybut-1,3-diene, 1.06 g of methyl orthoformate (trimethoxymethane) and 0.2 g of zinc chloride, and proceeds under the same conditions as in Example 3, the reaction time being 24 hours.

1.61 g of crude product are obtained, formed of 90% 2-bromo-5,5-dimethoxypent-2-enal and 10% 2-bromo-1,1,5,5-tetramethoxypent-2-ene, which corresponds to a yield of 72%. The structure of the product obtained is confirmed by NMR analysis and mass spectrometry.

EXAMPLE 6

Preparation of 2-bromo-5-hydroxyhex-2-enal

One starts with 2.21 g of 2-bromo-1-trimethylsiloxybut-1,3-diene, 0.44 g of ethanal and 0.1 g of zinc bromide and proceeds in the same manner as in Example 3, the reaction time being 3 hours.

1.74 g of crude product (95% purity) are obtained, representing a yield of 90%. The structure of the product obtained is confirmed by NMR and IR analysis.

We claim:

1. New dienoxysilanes having the general formula

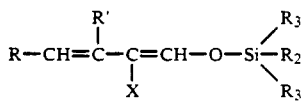

in which R designates a hydrogen atom, or a linear alkyl radical containing 1 to 4 carbon atoms, R' is a hydrogen atom or a methyl radical, each of $R_1$, $R_2$, $R_3$ designates an alkyl radical containing 1 to 4 carbon atoms or an aryl radical and X is a halogen atom, a dialkylamino radical each of the alkyl groups of which contains 1 to 4 carbon atoms, or a pyrrolidino, piperidino or morpholino radical, with the condition that R' can be a methyl radical only when R is a hydrogen atom.

2. A method of obtaining dienoxysilanes of claim 1, characterized by the fact that it consists in subjecting an α-substituted α-ethylene aldehyde of the formula

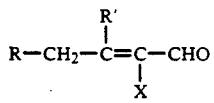

to the combined action of sodium iodide and a chlorosilane of the formula

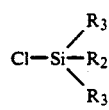

the different substituents of these two formulas satisfying the definitions indicated in claim 1, the reaction being carried out at room temperature, in anhydrous medium, in an inert atmosphere with agitation, in the presence of a weak base such as a tertiary amine, and the dienoxysilane being isolated from the reaction medium by extraction with a suitable nonpolar solvent.

3. A method according to claim 2, characterized by the fact that the reaction is carried out in anhydrous acetonitrile in the presence of triethylamine.

4. A method according to claim 2, characterized by the fact that the dienoxysilane is isolated from the reaction mixture by extraction with a solvent selected from the group consisting of petroleum ether, pentane, hexane and cyclohexane.

5. α-halo α-ethylene aldehydes obtained from dienoxysilanes forming the object of claim 1 and having the general formula:

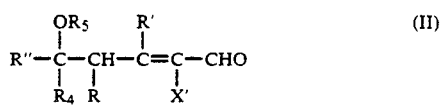

in which R is a hydrogen atom or a linear alkyl radical containing from 1 to 4 carbon atoms, R' is a hydrogen atom or a methyl radical, X' is a halogen atom, R" an alkyl, aryl or heteroaryl radical, an alkylethylene or arylethylene radical, or a methoxy or ethoxy radical, $R_4$ is a hydrogen atom or a methyl radical and $R_5$ is a hydrogen atom or a methyl or ethyl radical, with the condition that R' can be a methyl radical only when R is a hydrogen atom.

6. A method of obtaining α-halo α-ethylene aldehydes of claim 5, characterized by subjecting an aldehyde, an acetal or an orthoformate to the action of a halogenated dienoxysilane of the formula

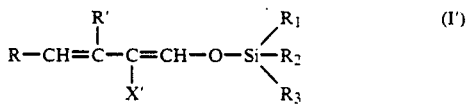

in which X' represents a halogen atom and the substituents R, R', $R_1$, $R_2$ and $R_3$ satisfy the definitions given in claim 1, the reaction being carried out at a temperature of 0° C. to 20° C. in an anhydrous solvent in an inert atmosphere in the presence of a Lewis acid catalyst, and the α-halo α-ethylene aldehyde being isolated from the reaction medium by addition of water, followed by separation of the aqueous phase, the organic phase being dried over anhydrous magnesium sulfate before evaporation of the solvent.

7. A method according to claim 6, characterized by the fact that the reaction is carried out in anhydrous dichloromethane in the presence of a catalyst selected from the group consisting of titanium tetrachloride, zinc dichloride and zinc dibromide.

8. A method according to claim 6 leading to the obtaining of an α-halo α-ethylene aldehyde of the formula

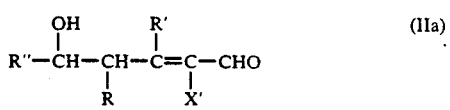

in which the substituents R, R', R" and X' satisfy the definitions given in claim 5, characterized by subjecting a dienoxysilane of formula I' to the action of an aldehyde of the formula R"CHO, the product obtained being, if necessary, subjected to hydrolysis directed at transforming the corresponding siloxane into α-halo α-ethylene aldehyde.

9. A method according to claim 6, leading to the obtaining of α-halo α-ethylene aldehyde of the formula

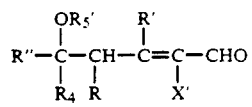
(IIb)

in which R′₅ is a methyl or ethyl radical and the substituents R, R′, R″, R₄ and X′ satisfy the definitions given in claim 5, characterized by subjecting a dienoxysilane of formula I′ to the action of an acetal of the formula

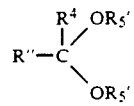

in which R′₅ is a methyl or ethyl radical and the substituents R″ and R₄ satisfy the definitions given in claim 5.

10. A method according to claim 6, leading to the obtaining of an α-halo α-ethylene aldehyde of the formula

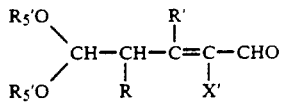
(IIc)

in which R′₅ is a methyl or ethyl radical and the substituents R, R′ and X′ satisfy the definitions given in claim 5, characterized by subjecting a dienoxysilane of formula I′ to the action of an orthoformate of the formula HC(OR′₅)₃ in which R′₅ is a methyl or ethyl radical.

* * * * *